(12) United States Patent
Birkett et al.

(10) Patent No.: US 7,361,365 B2
(45) Date of Patent: Apr. 22, 2008

(54) VERMIN REPELLENT

(75) Inventors: Mike Birkett, Harpenden (GB); Jan Pettersson, Uppsala (SE); John Picket, Harpenden (GB)

(73) Assignee: Organox AB, Ronninge (SE)

( * ) Notice: Subject to any disclaimer, the term of this patent is extended or adjusted under 35 U.S.C. 154(b) by 0 days.

(21) Appl. No.: 10/553,073

(22) PCT Filed: Apr. 12, 2004

(86) PCT No.: PCT/SE2004/000583

§ 371 (c)(1),
(2), (4) Date: Jul. 3, 2006

(87) PCT Pub. No.: WO2004/089090

PCT Pub. Date: Oct. 21, 2004

(65) Prior Publication Data

US 2007/0053941 A1   Mar. 8, 2007

(30) Foreign Application Priority Data

Apr. 12, 2003 (SE) .................... 0301100

(51) Int. Cl.
| | | |
|---|---|---|
| A01N 25/02 | (2006.01) | |
| A01N 25/08 | (2006.01) | |
| A01M 13/00 | (2006.01) | |
| A61K 31/497 | (2006.01) | |

(52) U.S. Cl. .............. 424/405; 424/409; 424/411; 514/252.1; 43/124; 43/125

(58) Field of Classification Search ............... 424/405, 424/409, 411; 514/252.1; 43/124, 125
See application file for complete search history.

(56) References Cited

FOREIGN PATENT DOCUMENTS

| WO | WO 85/05009 | * | 11/1985 |
|---|---|---|---|
| WO | WO 8505009 A1 | | 11/1985 |
| WO | WO 9404027 A1 | | 3/1994 |
| WO | WO 99/37152 | * | 7/1999 |
| WO | WO 9937152 A1 | | 7/1999 |

OTHER PUBLICATIONS

Leitner et al., 1990, Chemie, Mikrobiologie, Technologie der Lebensmittel, 12, 151-158 (abstract only cited).*

STN International, file CAPLUS, CAPLUS accession No. 1982:159586, Document No. 96:159586, Moore, B.P. et al.: "Identification of warning odor components, bitter principles and antifeedants in an aposematic beetle: Metriorrhynchus rhipidius (Coleoptera: Lycidae)"; & Insect Biochemistry (1981), 11(5), 493-9.

STN International, file CAPLUS, CAPLUS accession No. 1991:652102, Document No. 115:252102, Bestmann, H.J. et al.: "Plant insecticides. 9. Volatile constituents from Crotalaria ochroleuca and their effect on pest insects"; & Zeitschrift fuer Naturforschung, C: Journal of Biosciences (1991), 46(7-8), 579-84.

* cited by examiner

*Primary Examiner*—Ruth Davis
*Assistant Examiner*—Sheridan R MacAuley
(74) *Attorney, Agent, or Firm*—Bacon & Thomas PLLC

(57) ABSTRACT

A method for repelling a pest using 2-isopropyl-3-methoxipyrazine as a pest repellent, particularly a mole repellent, and a pest repelling composition which comprises this compound.

4 Claims, No Drawings

VERMIN REPELLENT

TECHNICAL FIELD

This invention relates in general to a pest repellent.

In this description and the enclosed claims, the term "pest" is used to designate animals that harm humans, domestic animals and crops or other resources used by humans. Although the invention relates to a general pest repellent, it will be described in detail with reference to animals belonging to the family *Talpidae*, particularly moles.

STATE OF THE ART

Mole (*Talpa europaea*) is a species belonging to the family *Talpidae*, which comprises about 30 species in the Northern hemisphere. The mole is 11 to 16 centimeters long and has a 2 to 5 centimeter long tail and short, silky, black fur. As an adaptation to life underground, external ears are absent, the eyes are tiny and the front feet greatly enlarged with long claws for digging. Moles are found in most of Europe, up to the southern part of Sweden, and in Western Asia. They are most common in deciduous woodland and grassland, often in gardens and golf courts, where the mole tunnels may undermine the land. Excess soil from the tunnels is transported to the soil surface through vertical tunnels, so that mole hills with a hole down the middle are formed. The mole hills are highly characteristic of the mole, and they function as an indicator of the presence of moles and an undermining of the land.

For example in gardens, moles can be controlled by water saturation of the soil, which forces the animals to leave the tunnels. The same effect can be achieved with smoke cartridges containing specific fumigation agents that are placed in the tunnels. It is also possible to set special traps. These are placed in the tunnels, but have to be searched and emptied daily according to present regulations.

The measures described are fairly drastic and risk affecting humans, other animals and the soil. As an example, a common fumigation agent contains aluminum phosphide (e.g. "Phost Fumitoxin"), which is toxic to humans and cannot be used in built-up areas. The smoke cartridges generally give rise to sulfur fumes that are relatively ineffective in controlling moles.

A great number of mole repellents are commercially available in the form of chemical compounds with a more or less repelling effect on moles that is supposed to make the animals abandon a given area.

An Internet search on mole repellents gives many hits, and many of the products contain secret formulas, for instance "Mole Repellent", "Whole Control Mole Spray", "Mole-Med" and "Mole-otov Cocktail". Other mole repellent descriptions comprise a declaration of contents, for instance "Shake Away", which is described as containing a mixture of urine from bobcat and fox.

The Hungarian patent HU 204 655 discloses a mole repellent comprising a number of chemical compounds, such as potassium chlorate, ammonium chloride, paraffin, naphthalene and crystallized sugar.

The Japanese patent JP 55040620 relates to a mole repellent which contains naphthalene and beta-naphtole as active substances.

The Japanese patent JP 61238707 discloses a mole repellent based on sulphamic acid and salts thereof.

The Japanese patent JP 62245508 relates to a mole repellent which is produced by reacting shikimic acid, toxin, amino acid and Kujin-alkaloid with mustard glycoside in water, alcohol, acetic acid and ethylene acetate and mixing of the reaction mixture with Kujin (the root of *Sophora angustifolia*), pyridine, starch, powder of Bansho (the fruit of *Capsicum annum*) and dehydrated Shikimi (*Illicum religiosum*) and chrysanthemum. The Japanese patent 3294208 discloses a mole repellent comprising wood vinegar, which is a fluid component produced by dry distillation of wood, or a mixture of wood vinegar and creosote oil.

The Japanese patent JP 6001705 discloses a mole repellent which contains a solid component (ammonium carbamate or ammonium carbonate) which emits gaseous ammonia in a reaction with air.

The state of the art shows that there is still a substantial need for a mole repellent which can be used in very small doses and is therefore not harmful to humans and other animals, is easy to apply, shows good effect, does not comprise a mixture of more or less harmful chemical products.

SHORT DESCRIPTION OF THE INVENTION

The present invention is based on the greatly surprising discovery that a pheromone from the ladybird, which is an attractant for both males and females of the Sevenspotted Lady Beetle, is an excellent mole repellent. The compound is 2-isopropyl-3-methoxy-pyrazine.

DETAILED DESCRIPTION OF THE INVENTION

The compound 2-isopropyl-3-methoxy-pyrazine ("IMP" in the following) has been identified by S. Al Abassi et al in *CMLS, Cell. Mol. Life Sci.* 54(1998) 876-879 as a pheromone in the Sevenspotted Lady Beetle (*Coccinella septempunctata*). The compound has also been identified as one of the compounds that gives Cheddar cheese its nutty flavour ("Characterization of volatile nutty flavor compounds in Cheddar cheese", M. A. Drake et al, *J. Anim. Sci.* Vol. 80, Suppl. 1/*J. Dairy Sci.* Vol. 85, Suppl. 1, Abstract 599).

Most surprisingly, it has been found that IMP is an excellent mole repellent and in a first aspect, the invention thus relates to the use of IMP as a pest repellent, in particular a mole repellent.

According to a second aspect, the invention relates to a pest repelling composition, in particular a mole repelling composition, which comprises the compound IMF and optional excipients, for example carriers, dilution agents, etc.

The compound IMF is commercially available for example from Sigma-Aldrich in the form of a clear fluid. It is also used in certain foodstuffs, such as spices.

One way to apply IMP is to introduce a pipe in the vertical part of a mole tunnel and to introduce several short pieces of tubing, for instance white laboratory tubing of pure latex, impregnated with IMP, into the pipe. These impregnated pieces of tubing could be a few centimeters long.

The invention is particularly useful for gardens, golf-courts and parks, where mole activity has been established through the presence of mole hills.

The invention has been described in further detail with reference to the mole as the pest, but the skilled artisan will realize that the invention is also useful for other pests, such as various rodents, particularly water voles.

The invention is illustrated by the following Examples.

EXAMPLE 1

Locality: A summer residence in Ängelholm in the south of Sweden.

Active substance: 100 μl 20% IMP in hexane in a sealed glass vial which was crushed at application in a mole tunnel.

| Time | Measure | Observed effect |
|---|---|---|
| Beginning of June | | about 20 mole hills |
| June 11 | 2 vials buried | |
| June 14 | 3 vials buried | |
| June 15 | | 4 new mole hills in direction from the vials |
| June 19 | | 2 new mole hills |
| June 23 | 1 vial buried | no mole hills on the lawn during the rest of the summer |
| January 2003 | | about 10 mole hills |

Comment on the observations: The observations show that IMP has a repelling effect on moles. The migration away after treatment and the migration back during late autumn 2002/winter 2003 coincides with the expected effect.

EXAMPLE 2

In a garden with an area of 700 square meters with notable mole activity, a zone with an area of 100 square meters was fenced in and treated with IMP under very favourable conditions.

After 4 days, 21 mole hills were observed in the treated area, as compared with 10 from the start, and in the untreated control area, 10 mole hills were observed, as compared with 6 from the start.

The results show that the moles were decidedly disturbed in the treated area, as they exhibited a more intense digging activity, resulting in more mole hills, to get away from the IMP fumes.

The invention claimed is:

1. A method of repelling moles which comprises administering to an area to be protected from the moles a composition comprising an effective amount of 2-isopropyl-3-methoxy-pyrazine to repel said moles.

2. The method according to claim 1, wherein the area to be protected contains mole tunnels and the composition is administered to said mole tunnels.

3. The method according to claim 2, wherein the composition is contained in a sealed glass vial which is placed in said tunnel and broken to release said composition.

4. The method according to claim 2, wherein the composition is impregnated in latex tubing which is placed in said tunnel.

* * * * *